United States Patent [19]

Roeschert et al.

[11] Patent Number: 5,314,786
[45] Date of Patent: May 24, 1994

[54] POSITIVE-WORKING RADIATION SENSITIVE MIXTURE COMPRISING SULFONIC ACID ESTERS OF 2,4,6-TRIS-(2-HYDROXYETHOXY)-[1,3,5]TRIAZINE, AND RECORDING MATERIAL CONTAINING THESE ESTERS

[75] Inventors: Horst Roeschert, ober-Hilbersheim; Georg Pawlowski, Wiesbaden; Juergen Fuchs, Wicker, all of Fed. Rep. of Germany

[73] Assignee: Hoechst Aktiengesellschaft, Frankfurt am Main, Fed. Rep. of Germany

[21] Appl. No.: 871,034

[22] Filed: Apr. 20, 1992

[30] Foreign Application Priority Data

Apr. 20, 1991 [DE] Fed. Rep. of Germany ....... 4112971

[51] Int. Cl.$^5$ .................. G03F 7/004; G03F 7/039
[52] U.S. Cl. .................................... 430/270; 430/281; 430/326; 430/920; 430/921; 522/50
[58] Field of Search ............... 430/270, 281, 915, 920, 430/921, 926, 326; 522/50

[56] References Cited

U.S. PATENT DOCUMENTS

| | | | |
|---|---|---|---|
| 3,779,778 | 12/1973 | Smith et al. | 96/115 R |
| 4,758,497 | 7/1988 | Shah et al. | 430/193 |
| 4,840,867 | 6/1989 | Elsaesser et al. | 430/156 |
| 5,118,582 | 6/1992 | Ueno et al. | 430/270 |
| 5,187,045 | 2/1993 | Bonham et al. | 430/275 |

FOREIGN PATENT DOCUMENTS

3930086A1 3/1991 Fed. Rep. of Germany.
3930087A1 3/1991 Fed. Rep. of Germany.

OTHER PUBLICATIONS

Tabata et al, "Polymers for Microelectronics–Science and Technology", 1989, pp. 66–67.
Houlihan et al., SPIE, Advances in Resist Technology and Processing, vol. 920, 1988.
Willson, "Organic Resist Materials—Theory, Materials and Processing", Series 219, 1983.

Primary Examiner—Marion E. McCamish
Assistant Examiner—Rosemary Ashton
Attorney, Agent, or Firm—Foley & Lardner

[57] ABSTRACT

A 2,4,6-tris-(2-hydroxyethoxy)-[1,3,5]triazine esterified with two or three arylsulfonic acids or heteroarylsulfonic acids is useful to prepare a positive-working radiation-sensitive mixture which is distinguished by a high resolution and a high sensitivity over a wide spectral range. It also shows high thermal stability and does not form corrosive photolysis products on exposure. A radiation-sensitive recording material which is produced from these esters is suitable for producing photoresists, electronic components, printing plates or for chemical milling.

20 Claims, No Drawings

POSITIVE-WORKING RADIATION SENSITIVE MIXTURE COMPRISING SULFONIC ACID ESTERS OF 2,4,6-TRIS-(2-HYDROXYETHOXY)-[1,3,5]TRIAZINE, AND RECORDING MATERIAL CONTAINING THESE ESTERS

BACKGROUND OF THE INVENTION

1. Field of the Invention

The present invention relates to sulfonic acid esters of 2,4,6-tris-(2-hydroxyethoxy)-[1,3,5]triazine and to a positive-working radiation-sensitive mixture, containing a) as a compound which generates a strong acid under the action of actinic radiation, the sulfonic acid ester b) a compound having at least one acid-cleavable C—O—C or C—O—Si bond and c) a polymeric binder which is insoluble in water and soluble or at least swellable in aqueous alkaline solutions.

The invention also relates to a radiation-sensitive recording material which is produced from these radiation sensitive mixtures and which is suitable for producing photoresists, electronic components, printing plates or for chemical milling.

2. Description of Related Art

Continuing reduction in the size of the structures, for example down into the range of less than 1 μm in chip manufacture, requires modified lithographic techniques. To form images of such fine structures, radiation of a short wavelength is used, such as high-energy UV light, electron beams and X-rays. The radiation-sensitive mixture must be adapted to short-wave radiation. A compilation of the requirements to be met by the radiation-sensitive mixture is given in the article by C. G. Willson "Organic Resist Materials - Theory and Chemistry" [Introduction to Microlithography, Theory, Materials, and Processing, editors L. F. Thompson, C. G. Willson, M. J. Bowden, ACS Symp. Ser., 219, 87 (1983), American Chemical Society, Washington].

There is therefore an increased demand for radiation-sensitive mixtures which can be used in the more recent technologies, such as mid-UV or deep-UV lithography [exposure, for example, with excimer lasers at wavelengths of 305 nm (XeF), 248 nm (KrF), 193 nm (ArF)], electron beam lithography or X-ray lithography, and which, furthermore, are preferably sensitive in a wide spectral region and correspondingly can also be used in conventional UV lithography.

Mixtures which, in addition to a binder insoluble in water and soluble or at least swellable in aqueous alkaline solutions and a component generating a strong acid under the action of actinic radiation, contain an acid-cleavable compound having, for example, C—O—C or C—O—Si bonds are described, for example, in DE-A 2,306,248 equivalent to U.S. Pat. No. 3,779,778.

Compounds which generate a strong acid on irradiation, especially onium salts, such as diazonium, phosphonium, sulfonium and iodonium salts of non-nucleophilic acids such as $HSbF_6$, $HAsF_6$ or $HPF_6$ as described by J. V. Crivello, Polym. Eng. Sci., 23 (1983) 953 have hitherto been used. In addition, halogen compounds, especially trichloromethyltriazine derivatives or trichloromethyloxadiazole derivatives, o-quinonediazidesulfonyl chlorides, o-quinonediazide-4-sulfonic acid esters, organometal/organohalogen combinations, bis(sulfonyl)diazomethanes, sulfonylcarbonyldiazomethanes (see DE-A 3,930,087) or nitrobenzyl tosylates (see F. M. Houlihan et al., SPIE Proc., Adv. in Resist Techn. and Proc. 920 (1988) 67) have been recommended.

These compounds are used in negative- or positive-working radiation-sensitive mixtures. The use of such photolytic acid generators involves, however, certain disadvantages which drastically restrict the possible uses thereof in various fields of application. For example, many of the onium salts are toxic, and their solubility is inadequate in many solvents, which is why only a few solvents are suitable for preparing a coating solution. Furthermore, when the onium salts are used undesired foreign atoms are sometimes introduced which can cause interference with the process, especially in microlithography. Moreover, the onium salts form Bronstedt acids, which have a very severe corrosive action in the photolysis. These acids attack sensitive substrates, so that the use of such mixtures leads to unsatisfactory results. The halogen compounds and also the quinonediazidesulfonic acid chlorides also form hydrohalic acids which have a severely corrosive action. In addition, such compounds also have only a limited storage life on certain substrates. This was improved by inserting an interlayer between the substrate and the radiation-sensitive layer containing compounds of the type (a), but this led to an undesired increase in defects and to diminished reproducibility, see DE-A 3,621,376 equivalent U.S. Pat. No. 4,840,867.

In more recent papers by F. M. Houlihan et al., SPIE 920, 67 (1988), it was shown by reference to positive-working systems that, in addition to the above-mentioned acid generators, nitrobenzyl tosylates, which on exposure also generate sulfonic acids having a low migration tendency, can be used in certain acid-unstable resist formulations. It can be deduced from these results that such compounds can also be used for photo-curable systems. However, the sensitivities thus achieved and the thermal stability of the photoresists proved to be inadequate.

Resist formulations with naphthoquinone-2-diazide-4-sulfonic acid esters, oximesulfonates, 1,2-disulfones, bis-sulfonyldiazomethane (see DE-A 3,930,086) and sulfonylcarbonyldiazomethane (see DE-A 3,930,087) have also been described. Under the action of actinic radiation, all these compounds form sulfonic acids which do not have a corrosive action. However, the photochemical reaction proceeds with an unsatisfactory quantum yield. The resist formulations absorb radiation of wavelength 248 nm to a considerable degree. The sensitivity to radiation of this wavelength is in the range from 50 to 100 $mJ/cm^2$. Images of structures having an order of magnitude of 0.5 μm and less cannot be formed by means of such resists.

It is also known from T. Ueno et al., Chemical Amplification Positive Resist Systems Using Novel Sulfonates as Acid Generators, in "Polymers for Microelectronics - Science and Technology", edited by Y. Tabata et al., Kodansha-Weinheim-New York, 1989, pages 66-67 to use 1,2,3-trihydroxybenzene fully esterified with methane-, ethane-, propane-, butane-, benzene-, toluene- or naphthalene-sulfonic acid as a photo-active acid generator in positive-working photoresist systems. However, these resist systems are not used in practice, since their thermal stability and plasma-etching resistance are inadequate and, after development, resist remnants in the grooves and unacceptable resist profiles are observed.

In spite of the intensive research activity so far carried out in this field, no radiation-sensitive mixture is at present known, by means of which a positive-working radiation-sensitive recording material can be produced which has a high sensitivity in the DUV region (200 to 300 nm) and high resolution, and which releases, even on short-time irradiation, a sufficient quantity of an acid which does not have a corrosive action and is strong enough to cleave compounds of type b), and which, in addition, can be developed in aqueous alkaline media.

SUMMARY OF THE INVENTION

It is therefore an object of the invention to propose a radiation-sensitive mixture based on acid-generating compounds in combination with acid-cleavable compounds, wherein the compound photolytically generating an acid should be as stable as possible on all known substrates and which gives an acid not having a corrosive action as the photoproduct.

It is a further object of the invention to provide a compound which generates a strong acid under the action of actinic radiation which can be used in the radiation-sensitive mixture, and to develop a method for producing such a compound.

It is a further object of the present invention to provide a recording material which has a high sensitivity in the DUV region and high resolution, and which is suitable for the production of photoresists, electronic components, and printed plates It is also an object of the present invention to provide a process for producing such a recording material, and to provide a method of preparing an image pattern with the use of the recording material.

In accomplishing the foregoing objectives, there has been provided, in accordance with one aspect of the present invention, a 2,4,6-tris-(2-hydroxyethoxy)[1,3,5]-triazine esterified with two or three acids selected from the group consisting of arylsulfonic acids, heteroarylsulfonic acids and mixtures thereof.

There has also been provided a positive-working radiation-sensitive mixture comprising a) a 2,4,6-tris-(2-hydroxyethoxy)-[1,3,5]triazine esterified with two or three acids selected from the group consisting of arylsulfonic acids, heteroarylsulfonic acids, and mixtures thereof, which generates a strong acid under the action of actinic radiation, b) at least one compound having at least one acid-cleavable C—O—C or C—O—Si bond and c) at least one polymeric binder which is insoluble in water and soluble or at least swellable in aqueous alkaline solutions.

There is further provided a positive-working radiation-sensitive recording material, comprising a support and a radiation-sensitive layer, wherein the layer comprises a positive-working mixture as described above.

There is further provided a method of producing such a recording material comprising dissolving said mixture in a solvent, applying the resulting solution to said support, and removing said solvent.

There is further provided a method of producing an image pattern comprising irradiating said radiation-sensitive layer imagewise, optionally heating the irradiated layer treating the layer with a developer which removes the irradiated areas of the layer, and optionally post-hardening the developed layer structures.

Further objects, features and advantages of the present invention will become apparent from the detailed description of preferred embodiments that follows.

DETAILED DESCRIPTION OF THE PREFERRED EMBODIMENTS

Any known arylsulfonic acid or heteroaryl sulfonic acids can be used to make the ester.

The arylsulfonic acids preferably have 6 to 10 aromatic carbon atoms. Examples of these are benzenesulfonic acid and the naphthalenesulfonic acids.

The heteroarylsulfonic acids preferably have, in addition to 4 to 9 carbon atoms, an aromatic oxygen or sulfur atom or 1 or 2 aromatic nitrogen atoms. Examples of these are the furan- and thiophene-sulfonic acids, and the pyrrole-, pyridine-, pyrimidine- and pyrazine-sulfonic acids. Sulfonic acids with a binuclear heteroaryl radical are also suitable. Of these, the benzofuran-, isobenzofuran-, benzo[b]thiophene- and indole-sulfonic acids are suitable. However, the nitrogen-containing heterocyclic compounds must not be basic, since, otherwise, the acid generated in the photoreaction is neutralized by the heterocyclic radical and, as a consequence of this, the efficiency of the acid-catalyzed reaction would be drastically reduced. Basicity is, for example, counterbalanced by appropriate substituents at nitrogen atoms.

The arylsulfonic acids and the heteroarylsulfonic acids may be substituted or unsubstituted. In principle, the substituents can be any which do not undergo undesired reactions during the use of the acids.

Suitable substituents include linear and branched alkyl groups preferably having not more than 8 carbon atoms, especially not more than 6 carbon atoms, such as methyl, ethyl, propyl, isopropyl, butyl, sec.-butyl, isobutyl and tert.-butyl. The alkyl groups can be fluorinated and preferably also perfluorinated. Of the perfluorinated alkyl radicals, trifluoromethyl and perfluorobutyl are particularly suitable. Further suitable substituents include ($C_1$-$C_8$)alkyl, ($C_1$-$C_8$)alkoxy, ($C_1$-$C_8$)alkanoyl, ($C_1$-$C_8$)alkanoyloxy, ($C_1$-$C_8$)alkanoylamino, ($C_6$-$C_{10}$)aryl, ($C_6$-$C_{10}$)aryloxy, ($C_6$-$C_{10}$)aryl-($C_1$-$C_8$)alkoxy, ($C_6$-$C_{11}$)aroylamino, ($C_6$-$C_{11}$)aroylamino-($C_1$-$C_8$)alkyl, cyano and halogen. More than one of these substituents may be present. Independently thereof, different substituents can be present side by side. Preferred substituents are ($C_1$-$C_4$)alkyl, ($C_1$-$C_4$)alkoxy and halogen.

A sulfonic acid ester of 3 mol of aryl and heteroarylsulfonic acid and 1 mol of 2,4,6-tris-(2-hydroxyethoxy)[1,3,5]triazine is generally preferred over a sulfonic acid ester of 2 mol of (hetero)arylsulfonic acid and 1 mol of 2,4,6-tris-(2-hydroxyethoxy)[1,3,5]triazine. Such a less extensively esterified product can, however, in special cases, show better solubility.

Particularly suitable aryl and heteroarylsulfonic acids are benzene-, 3-perfluorooctylbenzene-, 4-trifluoromethylbenzene-, 4-perfluorobutylbenzene-, toluene-4-, 4-bromobenzene-, 4-cyanobenzene-, 4-tert.-butylbenzene-, 2,4,5-trimethylbenzene-, 3,4-dichlorobenzene-sulfonic acids and 5-benzoylaminomethylthiophene-2-sulfonic acid.

The esters formed with the sulfonic acids are particularly suitable because they can be photolyzed with a high quantum yield but, at the same time, also possess sufficient thermal stability. The acid generated on photolysis is sufficiently strong to effect cross-linking of the cross-linkable components b) contained in the mixture according to the invention.

The preparation of the multifunctional sulfonic acid esters used in the mixture according to the invention is known per se. Any known method can be used. The starting materials used here are usually the corresponding sulfonic acid chlorides. Numerous examples of processes for preparing aromatic sulfonic acid esters are described, for example, by F. Muth in: Houben-Weyl-Miller, Methoden der organischen Chemie [Methods in Organic Chemistry], volume IX, page 633 (and references cited therein), Thieme-Verlag, 4th edition, Stuttgart 1955, and by S. Pawlenko, loc. cit., volume Ell, page 1084, Thieme-Verlag, 1st edition, Stuttgart 1985, and in the patent literature. The corresponding sulfonic acid anhydrides are also suitable starting materials (see S. Pawlenko, loc. cit., volume Ell, page 1086, Thieme-Verlag, 1st edition, Stuttgart 1985, and P. J. Stang, M. Hanack and L. R. Subramaniam, Synthesis, 1982, 85). This applies in particular to the benzenesulfonic acid anhydrides substituted by perfluoroalkyl groups.

The radiation-sensitive mixture according to the invention is distinguished by a high sensitivity over a wide spectral range. It shows high thermal stability and makes it possible to reproduce extremely fine structures of an original in true detail. The acid generated on irradiation does not have a corrosive action, so the mixture can also be used on sensitive substrate materials.

Surprisingly, the positive-working, radiation-sensitive mixtures according to the invention show not only a high thermal stability and plasma-etching resistance, but also outstanding lithographic properties which permit resolution in the half-micrometer range, and in some cases in the sub-half-micrometer range. After imagewise irradiation and subsequent development, an image of the mask in true detail is obtained. The resist fields have steep flanks. In the irradiated areas, the resist layer is completely detached, i.e., no remnants or residues of the layer remain on the substrate. The sulfonic acids generated in the photolysis lead to efficient cleavage of the resist component b), which permits the production of highly sensitive, positive-working mixtures.

Recording materials produced with the mixtures according to the invention show, surprisingly, an image differentiation which satisfies the most stringent requirements and, even more surprisingly, show an improvement in contrast and resolving power. For example, the mixtures according to the invention allow the production of a highly sensitive positive-working photoresist for high-energy UV2 radiation (for example 248 nm).

Since the mixture according to the invention is sensitive over a wide spectral range, any actinic radiation is generally suitable for imagewise irradiation. In this context, actinic radiation is to be understood as any radiation whose energy corresponds to at least that of short-wave visible light. In this case, UV radiation in the range from 190 to 450 nm, preferably from 200 to 400 nm, particularly preferably from 200 to 300 nm, and also electron beams or X-rays are particularly suitable.

The multifunctional sulfonic acid esters contained in the radiation-sensitive mixture according to the invention and generating an acid on irradiation can be used alone or in combination with other acid generators. Any other known additional acid generators or mixtures of these acid generators can be used. Suitable additional acid generators are especially the multifunctional sulfonic acid esters of aromatic polyhydroxy compounds, described in German patent Application P 41 12 973.3, which is equivalent to U.S. Ser. No. 07/870,905 filed concomitantly, which is hereby incorporated by reference.

Furthermore, the multifunctional sulfonic acid esters can be combined with onium salts, halogen compounds, especially trichloromethyltriazine derivatives or trichloromethyloxadiazole derivatives, 1,2-disulfones, o-quinonediazidesulfonyl chlorides or organometal/organohalogen combinations. Mixtures with bis(sulfonyl)-diazomethanes and sulfonyl-carbonyldiazomethanes are also possible. In such mixtures, however, the abovementioned disadvantages associated with the additional acid generator may reappear.

The content of multifunctional sulfonic acid esters in the mixture according to the invention may be varied depending on the desired use of the mixture and is in general 0.5 to 25% by weight, preferably 3 to 15% by weight, relative to the total weight of the solids in the mixture.

Any acid-cleavable compound having a cleavable C—O—C and/or C—O—Si bond can be used as component b) of the invention. The following classes of compounds have proved suitable as acid-cleavable compounds:

a) compounds having at least one orthocarboxylic acid ester group and/or carboxylic acid amideacetal group; these compounds also have a polymeric character and it is possible for the said groups to occur in the main chain or in side chains of the polymer (see DE-A 2,610,842 and 2,928,636), b) oligomeric or polymeric compounds with recurring acetal and/or ketal groups in the main chain (see DE-A 2,306,248 and 2,718,254), c) compounds having at least one enol ether group or N-acyliminocarbonate group (see EP-A 0,006,626 and 0,006,627), d) cyclic acetals or ketals of $\beta$-keto esters or $\beta$-keto amides (see EP-A 0,202,196), e) compounds having silyl ether groups (see DE-A 3,544,165 and 3,601,264), f) compounds having silylenol ether groups (see DE-A 3,730,785 and 3,730,783), g) monoacetals and monoketals of aldehydes and ketones respectively, having a solubility in the developer between 0.1 and 100 g/l (see DE-A 3,730,787), h) ethers based on tertiary alcohols (U.S. Pat. No. 4,603,101) and i) carboxylic acid esters and carbonates whose alcohol component is a tertiary alcohol, an allyl alcohol or a benzyl alcohol (see U.S. Pat. No. 4,491,628 and J. M. Fréchet et al., J. Imaging Sci. 30, 59–64 (1986)).

Mixtures of the above-mentioned acid-cleavable materials can also be used. However, an acid-cleavable material is preferred which can be assigned to only one of the above-mentioned types, in particular an acid-cleavable material having at least one acid-cleavable C—O—C bond, i.e., those materials are particularly preferred which belong to types (a), (b), (g) and (i). Under type (b), the polymeric acetals are preferred; and of the acid-cleavable materials of type (g) especially preferred are those which are derived from aldehydes or ketones having a boiling point above 150° C., preferably above 200° C. The N,O-polyacetals described in German Patent Application P 41 12 968.7, which is equivalent to U.S. Ser. No. 07/871,009 filed concomitantly and hereby incorporated by reference, are particularly preferred.

The content of the compound b) or the combination of compounds b) can vary over a wide range depending on the desired use of the mixture, and is generally 1 to 50% by weight, preferably 10 to 40% by weight, of the total weight of the solids in the radiation-sensitive mixture.

The radiation-sensitive mixture according to the invention also contains at least one polymeric binder c) which is insoluble in water, but soluble or at least swellable in aqueous alkaline solutions. Any binder or combination of binders may be used which have these characteristics. The binder is in particular distinguished by good compatibility with the other constituents of the radiation-sensitive mixture and especially by the lowest possible characteristic absorption, i.e., a high transparency, in the wavelength range from 190 to 300 nm.

Binders based solely on novolak condensation resins, which are generally used in combination with naphthoquinone-diazides as photoactive components, do not meet this condition. Although novolak condensation resins show in the unexposed areas a decrease in the solubility in aqueous alkaline developers after imagewise exposure, their characteristic absorption in the range of the short wavelength desired for the irradiation is undesirably high.

However, novolak condensation resins can be used in a mixture with other resins of higher transparency, the other resins being suitable as binders in and of themselves. The mixing ratios here depend predominantly on the nature of the binder to be mixed with the novolak resin. Especially important factors are the degree of characteristic absorption of the binder in the said wavelength range, and also the miscibility with the other constituents of the radiation-sensitive mixture. In general, however, the binder of the radiation-sensitive mixture according to the invention preferably contains at most 30% by weight, especially at most 20% by weight, of a novolak condensation resin.

Suitable binders are homopolymers or copolymers of 4-hydroxystyrene and alkyl derivatives thereof, for example of 3-methyl-4-hydroxystyrene, and homopolymers or copolymers of other vinylphenols, for example of 3-hydroxystyrene or esters or amides of crylic acid with aromatics containing phenolic groups. Polymerizable compounds such as styrene, methyl (meth)acrylate or the like can be used as comonomers.

Mixtures having an increased plasma resistance are obtained when silicon-containing vinyl monomers, for example vinyltrimethylsilane, are also used for the preparation of the binders. The transparency of these binders in the region of interest is in general higher, so that improved structuring is possible.

Homopolymers or copolymers of maleimide can also be used. These binders also show a high transparency in the wavelength range described. Here again, the comonomers preferably used are styrene, substituted styrenes, vinyl ethers, vinyl esters vinylsilyl compounds or (meth)acrylates.

Finally, copolymers of styrene can be used with comonomers which effect an increase in solubility in aqueous alkaline solutions. These include, for example, maleic anhydride and maleic acid half-esters.

The said binders can be mixed if this does not impair the optical quality of the radiation-sensitive mixture. However, binder mixtures are not preferred.

Any amount of binder can be used depending on the desired utility of the mixture. The binder content is in general 40 to 95% by weight, especially 50 to 90% by weight, relative to the total weight of the solid constituents of the radiation-sensitive mixture. The binder preferably has an extinction of less than 0.5 $\mu$m, more preferably less than 0.3 $\mu$m, for radiation of wavelength about 248 nm.

The glass transition temperature of the binder or the combination of binders is preferably around at least 120° C.

If appropriate, one or more additive such as dyes, pigments, plasticizers, wetting agents and flow agents, polyglycols and cellulose ethers, for example ethylcellulose, can also be added to the radiation-sensitive mixtures according to the invention in order to meet special requirements, such as flexibility, adhesion and gloss.

Any known substrate can be coated with the mixture, and any known process can be used to perform the coating. Generally, when a substrate is to be coated, the radiation-sensitive mixture according to the invention is expediently dissolved in a solvent or in a combination of solvents. Ethylene glycol and propylene glycol and the monoalkyl and dialkyl ethers derived from them, especially the monomethyl and dimethyl ethers and the monoethyl and diethyl ethers, esters derived from aliphatic ($C_1$–$C_6$)carboxylic acids and ($C_1$–$C_8$)alkanols or ($C_1$–$C_8$)alkanediols or ($C_1$–$C_6$)alkoxy-($C_1$–$C_8$)alkanols, for example ethyl acetate, hydroxyethyl acetate, alkoxyethyl acetate, n-butyl acetate, propylene glycol monoalkyl etheracetate, especially propylene glycol methyl etheracetate and amyl acetate, ethers such as tetrahydrofuran and dioxane, ketones such as methyl ethyl ketone, methyl isobutyl ketone, cyclopentanone and cyclohexanone, N,N-dialkyl-carboxylic acid amides such as N,N-dimethylformamide and N,N-dimethylacetamide, and also hexamethylphosphotriamide, N-methyl-pyrrolidin-2-one and butyrolactone, and also any desired mixtures of these, are particularly suitable for this purpose. Among these, the glycol ethers, aliphatic esters and ketones are particularly preferred.

Ultimately, the choice of the solvent or solvent mixture depends on the coating process used, on the desired layer thickness and on the drying conditions. The solvents must also be chemically inert to the other layer constituents under the conditions used.

The solution prepared with the said solvents generally has a solids content from 5 to 60% by weight, preferably up to 50% by weight.

Finally, the invention also relates to a radiation-sensitive recording material which comprises a substrate and, preferably located adjacent to the substrate, a radiation-sensitive layer containing the mixture according to the invention.

Possible substrates are all those materials of which capacitors, semiconductors, multi-layer printed circuits or integrated circuits are composed, or from which these can be produced. Silicon substrates which can also be thermally oxidized and/or coated with aluminum and also doped merit special mention. In addition, all other substrates usual in semiconductor technology are possible, such as silicon nitride, gallium arsenide and indium phosphide. Moreover, the substrates known from liquid crystal display manufacture are possible, for example glass or indium-tin oxide, and also metal plates and foils, for example foils of aluminum, copper, or zinc, bimetal and trimetal foils, and also electrically nonconductive foils on which metals have been vapor-deposited, and paper. These substrates can be thermally pretreated, superficially roughened, incipiently etched or pretreated with chemicals to improve desired properties, for example to enhance the hydrophilic character.

To impart better cohesion and/or better adhesion of the radiation-sensitive layer to the substrate surface, the layer can contain an adhesion promoter. In the case of silicon or silica substrates, adhesion promoters of the aminosilane type, for example 3-aminopropyltriethoxysilane or hexamethyldisilazane, can be used for this purpose. Furthermore, the substrate can be coated with an adhesion promoting layer prior to application of the radiation-sensitive mixture.

Suitable supports for the production of photomechanical recording layers, such as printing forms for letterpress printing, planographic printing, screen printing and flexographic printing, are in particular aluminum plates, which may have been anodically oxidized, grained and/or silicated beforehand, zinc and steel plates which may be chromium-plated, and plastic films and paper.

The recording material according to the invention is exposed imagewise to actinic radiation. Suitable radiation sources are especially metal halide lamps, carbon arc lamps, xenon lamps and mercury vapor lamps. Likewise, exposure can be carried out with high-energy radiation such as laser radiation, electron beams or X-rays. However, lamps which can emit light of a wavelength from 190 to 260 nm, i.e., especially xenon lamps and mercury vapor lamps, are particularly preferred. Furthermore, laser light sources can also be used, for example excimer lasers, especially KrF or ArF lasers, which emit at 248 and 193 nm respectively. The radiation sources must show adequate emission in the said wavelength ranges.

The thickness of the light-sensitive layer depends on the intended use. In general, it is between 0.1 and 100 $\mu$m, preferably between 0.5 and 10 $\mu$m, particularly preferably about 1.0 $\mu$m. Preferably the radiation-sensitive layer at a thickness of 1.0 $\mu$m has an extinction of less than 0.75, preferably less than 0.50 and particularly preferably less than 0.35, for radiation of wavelength 248 nm.

The invention also relates to a process for producing a radiation-sensitive recording material. The radiation-sensitive mixture can be applied to the substrate in any known manner, such as by spraying, flow-coating, rolling, whirler-coating and dip-coating. The solvent is then removed by evaporation so that the radiation-sensitive layer remains on the surface of the substrate. The removal of the solvent can be promoted by heating the layer to temperatures of up to 150° C. The mixture can, however, also be first applied in the above-mentioned way to a temporary support from which it is transferred under pressure and at an elevated temperature to the final support material. The materials used as temporary support can in principle be all those which are also suitable as support materials. Subsequently, the layer is irradiated imagewise. The layer is then treated with a developer solution which dissolves and removes the irradiated areas of the layer so that an image of the original used in the imagewise irradiation remains on the substrate surface.

Any known developer can be used. Suitable developers are especially aqueous solutions which contain silicates, metasilicates, hydroxides, hydrogen phosphates and dihydrogen phosphates, carbonates or hydrogen carbonates of alkali metal ions, alkaline earth metal ions and/or ammonium ions, and also ammonia and the like. Metal ion-free developers are described in U.S. Pat. No. 4,729,941, EP-A 0,062,733, U.S. Pat. Nos. 4,628,023, 4,141,733, EP-A 0,097,282 and EP-A 0,023,758. The content of these substances in the developer solution is in general 0.1 to 15% by weight, preferably 0.5 to 5% by weight, relative to the weight of the developer solution. Preferably, metal ion-free developers are used. Small quantities of a wetting agent can also be added to the developers in order to facilitate the detachment of the soluble areas of the layer.

The developed layer structures can be post-hardened. This is effected in any known manner, in general by heating on a hotplate up to a temperature below the flow temperature and subsequently exposing the whole area to the UV light from a xenonmercury vapor lamp (range from 200 to 250 nm). As a result of the post-hardening, the image structures are cross-linked, so that in general they have a flow resistance up to temperatures of more than 200° C. The post-hardening can also be effected without a temperature increase solely by irradiation with high-energy UV light.

The radiation-sensitive mixture according to the invention can be used in the production of integrated circuits or of discrete electrical components by lithographic processes, since it shows a high light sensitivity, especially in the case of irradiation with light of a wavelength between 190 and 300 nm. Since the mixtures bleach very well on exposure, finer structures can be achieved than are possible with the known mixtures. The developed resist layer serves as a mask for the subsequent process steps. Examples of such steps are the etching of the layer support, the implantation of ions into the layer support or the precipitation of metals or other materials on the layer support.

The examples described below illustrate the invention without restricting it.

SYNTHESIS EXAMPLE 2,4,6-Tris-[2-(toluene-4-sulfonyloxy)-ethoxy]-[1,3,5]triazine 73.8 g (380 mmol) of p-toluenesulfonic acid chloride were added in the course of 10 minutes at 0° C. to a solution of 20.0 g (76.5 mmol) of 2,4,6-tris-(2-hydroxyethoxy)[1,3,5]triazine and 60.6 g (760 mmol) of pyridine in 400 ml of dry acetonitrile, and the mixture was stirred for 4 hours at 0° C. The ice bath was then removed, and the mixture was allowed to warm to room temperature. It was then slowly added dropwise with continuous stirring to 300 ml of ice-water and then extracted with 400 ml of dichloromethane. The organic phase was washed several times with a saturated aqueous sodium sulfate solution and dried with sodium sulfate. The solvent was then distilled off in vacuo. The residue was taken up in 500 ml of dichloromethane, washed with 3×150 ml of 3N aqueous hydrochloric acid and with 2×150 ml of saturated aqueous sodium sulfate solution and subsequently dried with magnesium sulfate. The solvent was again distilled off in vacuo. The last volatile constituents were removed in a high vacuum and the residue solidified with foaming up. This gave 36.5 g (67%) of an almost colorless powder.

Recrystallization from an isopropanol/acetone solvent mixture gave a colorless powder having a melting point of 111° C.

The analysis of this compound gave the following values:

Calculated: C 49.78%; H 4.60%; N 5.81%; S 13.29%.
Found: C 49.3%; H 4.4%; N 5.6%; S 13.4%.

The sulfonic acid esters of 2,4,6-tris-(2-hydroxyethoxy)-[1,3,5]triazine were characterized by $^1$H and $^{13}$C high-field nuclear magnetic resonance spectra, by elemental analyses and by thin-layer chromatography (to prove the absence of unconverted sulfonic acid chloride) and, if appropriate, by IR spectroscopy (to prove the absence of free hydroxy groups in the product).

APPLICATION EXAMPLES

The following examples 1 to 6 demonstrate the suitability of the mixture according to the invention for recording materials in microlithography. The superiority of the mixtures according to the invention over those from the state of the art is shown by reference to Comparison Examples 7 and 8. In the examples below, p.b.w. means parts by weight.

EXAMPLE 1

A coating solution was prepared from
4.5 p.b.w. of a homopolymer of 3-methyl-4-hydroxystyrene having a softening range of about 155° C. and a mean molecular weight of about 25,000 [determined by gel permeation chromatography (GPC)],
3.0 p.b.w. of an N,O-polyacetal prepared from benzaldehyde dimethylacetal and 2-hydroxyethyl N-propylcarbamate analogously to Preparation Example 1 of German Patent Application P 41 12 968.7 which is equivalent to U.S. Ser. No. 07/871,009 filed concomitantly, and which is hereby incorporated by reference and
0.8 p.b.w. of 2,4,6-tris-[2-(4-bromobenzenesulfonyloxy)-ethoxy]-[1,3,5]triazine (prepared analogously to the Synthesis Example) in
42 p.b.w. of propylene glycol monomethyl etheracetate.

The coating solution was filtered through a filter of 0.2 μm pore diameter and whirler-coated onto a wafer pretreated with an adhesion promoter (hexamethyldisilazane). The whirler speed of rotation was here selected such that layer thicknesses of about 1.07 μm were obtained after drying at 110° C. for 1 minute on a hotplate.

The recording material was exposed imagewise under an original to the radiation of a KrF-excimer laser (248 nm) with an energy of 18 mJ/cm$^2$ and then subjected to a post-exposure bake on a hotplate for 1 minute at 80° C.

The recording material was developed using 0.27N aqueous tetramethylammonium hydroxide solution.

After a developing time of 60 seconds, a defect-free, positive image of the mask with steep resist flanks was obtained. Even structures of a size of 0.5 μm and less were resolved in true detail. An examination by scanning electron microscopy of the flanks of the resist profiles proved that these were aligned virtually perpendicular to the substrate surface.

The radiation-sensitive recording materials described in Examples 2 to 6 also gave a defect-free image of the mask with steep resist flanks, and even structures of a size of 0.5 μm and less were resolved in true detail. The resist flanks were in all cases aligned almost perpendicularly to the substrate surface. The triazine derivatives were prepared according to or analogously to the Synthesis Example.

EXAMPLE 2

A coating solution was prepared from
4.5 p.b.w. of a 3-methyl-4-hydroxystyrene/p-hydroxystyrene copolymer (molar ratio 75:25) having a mean molecular weight of about 28,000 (GPC),
3.0 p.b.w. of an O,O-polyacetal prepared from benzaldehyde dimethylacetal and a tricyclo[5.2.1.0$^{2,6}$]decanediyl-bis-methanol ("TCD alcohol" isomer mixture) prepared analogously to Preparation Example 1 of DE-A 3,730,787, which is hereby incorporated by reference, and
1.0 p.b.w. of 2,4,6-tris-[2-(toluene-4-sulfonyloxy)ethoxy]-[1,3,5]triazine in 42 p.b.w. of propylene glycol monomethyl ether-acetate.

Coating, drying and development conditions were the same as in Example 1.

The recording material was exposed imagewise under an original to the radiation of a xenon-mercury vapor lamp at 260 nm (with an interference filter) with an energy of 23 mJ/cm$^2$ and developed for 60 seconds.

EXAMPLE 3

A wafer produced according to Example 2 was irradiated under an original with the radiation of a KrF-excimer laser at a wavelength of 248 nm with an energy of 24 mJ/cm$^2$. After development, a true image of the original was obtained similarly to Example 2, in which even structures in the sub-half micrometer range were reproduced in true detail.

EXAMPLE 4

A coating solution was prepared from
6.0 p.b.w. of a 3-methyl-4-hydroxystyrene homopolymer having a softening range of about 155° C.,
2.5 p.b.w. of terephthaldialdehyde tetra(phenoxyethyl)-diacetal, prepared analogously to Preparation Example 1 of DE-A 3,730,787, and
0.7 p.b.w. of 2,4,6-tris-[2-(4-trifluoromethylbenzenesulfonyloxy)-ethoxy]-[1,3,5]triazine in
42 p.b.w. of propylene glycol monomethyl etheracetate.

As described in Example 1, the solution was pretreated, whirled on and dried at 115° C. for 1 minute. The recording material was exposed imagewise under an original to the radiation of a xenon-mercury vapor lamp at 260 nm (with an interference filter) with an energy of 27 mJ/cm$^2$ and dried at 75° C. for 1 minute. Development was done as in Example 1, and the exposed areas being detached without residues within 60 seconds.

EXAMPLE 5

A coating solution was prepared as described in Example 1, but with the modification that, in place of the N,O-polyacetal as the acid-unstable component and instead of the 2,4,6-tris-[2-(4-bromobenzenesulfonyloxy)ethoxy][1,3,5]triazine used therein,
3.0 p.b.w. of an N,O-polyacetal prepared from benzaldehyde dimethylacetal and 2-hydroxyethyl N-hexylcarbamate and
0.8 p.b.w. of 2,4,6-tris-[2-(4-bromobenzenesulfonyloxy)-ethoxy]-[1,3,5]triazine
were used. The solution was pretreated, whirled on and dried as in Example 1, and the recording material was exposed imagewise with an energy of 17 mJ/cm$^2$. After the post-exposure bake, development was carried out as in Example 1, and the exposed areas were detached without residues within 55 seconds.

EXAMPLE 6

A coating solution was prepared as in Example 2, but with the modification that 0.8 p.b.w. of 2,4,6-tris-[2-(3,5-bis-trifluoromethylbenzenesulfonyloxy)-ethoxy][1,3,5]-triazine was employed in place of the 2,4,6-tris[ 2-(toluene-4-sulfonyloxy)-ethoxy]-[1,3,5]triazine used therein as photoactive acid generator.

The solution was pretreated, whirled on and dried as described in Example 2, and the recording material was exposed imagewise with an energy of 26 mJ/cm$^2$. After the post-exposure bake, development was carried out as in Example 2, and the exposed areas were detached without residues within 70 seconds.

EXAMPLES 7 AND 8 (COMPARATIVE EXAMPLES)

The resist formulation of Example 2 was modified in such a way that the acid-generating compound used therein was replaced by the same quantity of triphenylsulfonium hexafluoroantimonate (Example 7) or 2,1-diazonaphthoquinone-4-sulfonic acid ester of 2-ethoxyethyl 4,4'-bis(4-hydroxyphenyl)-valeriate (Example 8) respectively.

After exposure to radiation of a wavelength of 260 nm (xenon-mercury vapor lamp) and an energy of 21 mJ/cm$^2$ (Example 7) or 84 mJ/cm$^2$ (Example 8) and development using 0.27N aqueous tetramethylammonium hydroxide solution, structures were obtained which did not show any image differentiation useful in practice. In both cases, structures having a so-called "coating foot" were obtained, i.e., residues of the resist adhered to the substrate in the exposed areas. In addition, the resolution and line profile were unsatisfactory. Even with the use of optimized baking and developing conditions, it was not possible to obtain results leading to acceptable structurings.

What is claimed is:

1. A positive-working radiation-sensitive mixture comprising
   a) a 2,4,6-tris-(2-hydroxyethoxy)-[1,3,5]triazine esterified with two or three acids selected from the group consisting of arylsulfonic acids, heteroarylsulfonic acids, and mixtures thereof, which generates a strong acid under the action of actinic radiation,
   b) at least one compound having at least one acid-cleavable C—O—C or C—O—Si bond and
   c) at least one polymeric binder which is insoluble in water and soluble or at least swellable in aqueous alkaline solutions.

2. A positive-working radiation-sensitive mixture as claimed in claim 1, wherein a least one of the sulfonic acids is an arylsulfonic acid having 6 to 10 aromatic carbon atoms.

3. A positive-working radiation-sensitive mixture as claimed in claim 1, wherein at least one of the sulfonic acids is a heteroarylsulfonic acid having 4 to 9 carbon atoms and 1 aromatic oxygen or sulfur atom, or 1 or 2 aromatic nitrogen atoms.

4. A positive-working radiation-sensitive mixture as claimed in claim 1, wherein at least one of the sulfonic acids are substituted by at least one of (C$_1$-C$_8$)alkyl, (C$_1$-C$_8$)alkoxy, (C$_1$-C$_8$)alkanoyl, (C$_1$-C$_8$)alkanoyloxy, (C$_1$-C$_8$)alkanoylamino, (C$_6$-C$_{10}$)aryl, (C$_6$-C$_{10}$)aryloxy, (C$_6$-C$_{10}$)aryl-(C$_1$-C$_8$)alkoxy, (C$_6$-C$_{11}$)aroylamino(C$_1$-C$_8$)alkyl, (C$_6$-C$_{11}$)aroylamino, cyano, or halogen.

5. A positive-working radiation-sensitive mixture as claimed in claim 1, wherein the compound a) generates an acid under the action of radiation of 190 to 450 nm wavelength.

6. A positive-working radiation-sensitive mixture as claimed in claim 1, wherein c) comprises a polymer which contains at least one phenolic hydroxy group.

7. A positive-working radiation-sensitive mixture as claimed in claim 6, wherein said polymer is a substituted or unsubstituted poly(hydroxystyrene).

8. A positive-working radiation-sensitive mixture as claimed in claim 6, wherein said polymer is a polymer containing a (meth)acrylic acid esterified with a compound which, in addition to the hydroxy group required for ester formation, contains at least one free, phenolic hydroxy group.

9. A positive-working radiation-sensitive mixture as claimed in claim 6, wherein c) has an extinction of less than 0.5 $\mu$m$^{-1}$ for radiation having a wavelength of about 248 nm.

10. A positive-working radiation-sensitive mixture as claimed in claim 1, comprising 40 to 95% by weight of c) based on the total weight of the solids in the radiation-sensitive mixture.

11. A positive-working radiation-sensitive mixture as claimed in claim 1, comprising 1 to 50% by weight of b) based on the total weight of solids in the radiation-sensitive mixture.

12. A method of producing a recording material as claimed in claim 11 which comprises applying said radiation-sensitive layer to said support.

13. A positive-working radiation-sensitive mixture as claimed in claim 1, comprising 0.5 to 25% by weight of a) based on the total weight of the solids in the radiation-sensitive mixture.

14. A positive-working radiation-sensitive recording material, comprising a support and a radiation-sensitive layer, wherein the layer comprises a positive-working mixture as claimed in claim 1.

15. A positive-working radiation-sensitive recording material as claimed in claim 14, wherein the radiation-sensitive layer at a thickness of 1.0 $\mu$m has an extinction of less than 0.75 for radiation of wavelength 248 nm.

16. A method for producing an image pattern comprising dissolving the mixture of claim 1 in a solvent, applying the resulting solution to a support so as to form a radiation-sensitive layer on the support, removing said solvent, irradiating said radiation-sensitive layer imagewise, optionally heating the irradiated layer, treating the layer with a developer which removes the irradiated areas of the layer, and optionally post-hardening the developed layer structures.

17. A positive-working radiation-sensitive mixture as claimed in claim 1, wherein the ester a) is completely esterified.

18. A positive-working radiation-sensitive mixture as claimed in claim 1, wherein the ester a) is partially esterified.

19. A positive-working radiation-sensitive mixture as claimed in claim 1, wherein the binder comprises a polymer of 3-methyl-4-hydroxy styrene and wherein the binder comprises at most 20% by weight of a novolak resin.

20. A positive-working radiation-sensitive mixture as claimed in claim 1, wherein b) comprises an N,O-polyacetal or an O,O-polyacetal.

* * * * *